United States Patent [19]
Greene et al.

[11] Patent Number: 6,027,462
[45] Date of Patent: Feb. 22, 2000

[54] METHOD AND APPARATUS FOR DEFLECTING A SCREW-IN-LEAD

[75] Inventors: Corinne A. Greene, Roseville; Kenneth C. Gardeski, Plymouth; Andrzej Malewicz, Minneapolis; Brett R. Johnson, St. Paul, all of Minn.

[73] Assignee: Medtronic, Inc., Minneapolis, Minn.

[21] Appl. No.: 09/126,569

[22] Filed: Jul. 30, 1998

[51] Int. Cl.$^7$ ........................................................ A61B 5/00
[52] U.S. Cl. ............................................................. 600/585
[58] Field of Search ................................... 600/434, 435, 600/585; 33/511, 512

[56] References Cited

U.S. PATENT DOCUMENTS

| | | | |
|---|---|---|---|
| 4,136,703 | 1/1979 | Wittkampf | 128/419 P |
| 4,488,561 | 12/1984 | Doring | 128/786 |
| 4,572,605 | 2/1986 | Hess | 339/177 R |
| 4,676,249 | 6/1987 | Arenas et al. | 128/657 |
| 4,815,478 | 3/1989 | Buchbinder et al. | 128/772 |
| 4,922,607 | 5/1990 | Doan et al. | 29/879 |
| 4,940,062 | 7/1990 | Hampton et al. | 128/772 |
| 5,040,543 | 8/1991 | Badera et al. | 128/772 |
| 5,170,787 | 12/1992 | Lindegren | 128/642 |
| 5,327,906 | 7/1994 | Fideler | 128/772 |
| 5,473,812 | 12/1995 | Morris et al. | 29/825 |
| 5,662,119 | 9/1997 | Brennen et al. | 128/772 |
| 5,728,148 | 3/1998 | Bostrom et al. | 607/116 |

*Primary Examiner*—Max Hindenburg
*Attorney, Agent, or Firm*—Reed A. Duthler; Harold R. Patton

[57] ABSTRACT

An apparatus for deflecting a catheter or lead, for example a deflectable stylet or guidewire. The device includes an outer tubular member, a tension member mounted within the outer tubular member and coupled to the outer member and a handle mounted at the proximal end of the tubular member. The handle includes a major handle portion which has a rotatable knob located at its distal end, surrounding a proximal portion of the outer tubular member and provided with inwardly directed threading and an inner slider member provided with outwardly directed threading engaging the inwardly directed threading of the knob. The slider is advanced or retracted longitudinally within the handle by rotation of the knob but is rotationally fixed with regard to the major handle portion. The outer tubular member is engaged at its proximal end with the inner slider member and the tension wire is fixedly engaged with the major handle portion, whereby rotation of the knob results in advancement or retraction of the outer tubular member relative to the tension wire and the major portion of the handle, which in turn causes the deflection of the outer tubular member.

5 Claims, 4 Drawing Sheets

METHOD AND APPARATUS FOR DEFLECTING A SCREW-IN-LEAD

CROSS REFERENCE TO CO-PENDING PATENT APPLICATION

Reference is made to commonly assigned U.S. patent application Ser. No. 09/087,482, filed May 29, 1998 by Baumann for a "Method and Apparatus for Deflecting a Catheter or Lead", which has related subject matter.

BACKGROUND OF THE INVENTION

The present invention relates generally to implantable leads and catheters and more particularly to mechanisms for deflecting implantable leads and catheters to assist in guiding them through the vascular system.

Over the years, quite a number of mechanisms have been disclosed and employed to deflect catheters and implantable leads. These have taken the form of deflectable guidewires and deflectable stylets, typically operable from the proximal end of the lead or catheter, which controllably impart a curve to the distal portion of the catheter. One group of devices comprise deflectable stylets or guidewires which employ a straight, tubular outer member with a curved inner member, the inner and outer members movable relative to one another. Examples of this type of deflection mechanism are disclosed in U.S. Pat. No. 4,136,703 issued to Wittkampf and U.S. Pat. No. 5,728,148 issued to Bostrom et al. Alternatively, deflection devices employing a curved outer member and a relatively straight inner member are also known to the art, as disclosed in U.S. Pat. No. 4,676,249 issued to Arenas and U.S. Pat. No. 5,040,543 issued to Badera et al. In devices of both types, the relative position of the inner member with respect to the outer member determines the degree to which the curved member (inner or outer) is allowed to display its preset curvature.

A more commonly employed approach to providing controllable deflection employs a generally straight outer member and a tension or push wire located within the outer member which on advancement or retraction causes the outer member to bend. Examples of such deflection mechanisms can be found in U.S. Pat. No. 4,815,478 issued to Buchbinder et al., and U.S. Pat. No. 4,940,062 issued to Hampton et al.

Particularly in the context of deflectable stylets intended for use in conjunction with implantable medical leads such as pacing and cardioversion leads, steerable stylets employing this third type of deflection mechanism are disclosed in U.S. Pat. No. 5,662,119 issued to Brennan et al., U.S. Pat. No. 5,170,787 issued to Lindegren, and U.S. Pat. No. 5,327,906 issued to Fideler et al, all of which are incorporated herein by reference in their entireties.

While all of the mechanisms disclosed in the above cited prior art patents are at least to some degree workable, there remains a need for a deflectable stylet or guidewire which is particularly optimized for use with fixed-screw pacing leads.

BACKGROUND OF THE INVENTION

The present invention is directed toward providing a deflectable stylet which is readily operable to allow advancement of a fixed-screw pacing lead and screwing the helical electrode thereon into heart tissue. The present invention accomplishes these goals by means of an optimized control handle assembly which includes a deflection control, preferably a rotatable and slidable knob, mounted to the distal end of a handle. The handle includes a proximal portion having an enlarged diameter and a distal portion having a reduced diameter, corresponding to the diameter of the proximal portion of the deflection control. The handle is of sufficient length that it will extend across the width of at least three fingers of a typical physician's hand, and the reduced diameter portion of the handle in conjunction with the portion of the deflection control having a similar diameter are together of sufficient length that to extend across the width of at least two fingers of a typical physician's hand.

The deflection control is movable rotationally and/or longitudinally relative to the handle portion to cause deflection of the stylet. The control portion is manipulated by the physician's thumb and forefinger while the palm and the other three fingers of the physician's hand encircle the handle portion. The control handle is grasped in this fashion as the lead is advanced to its desired location, making use of the ability of the stylet to deflect the lead when necessary. When the lead is properly located, the physician's hand is moved distally so that the physician's thumb and forefinger extend distally beyond the control portion and may be employed to rotate the lead around the deflectable stylet. The physician's palm and index and ring fingers encircle at least the proximal portion of the deflection control and the distal portion of the handle, which in turn keeps the control and handle portions in fixed relationship with one another, maintaining the curvature and orientation of the stylet as the lead is rotated around the stylet to screw the helical electrode into body tissue.

DETAILED DESCRIPTION OF THE PREFERRED EMBODIMENTS

Figure 1:
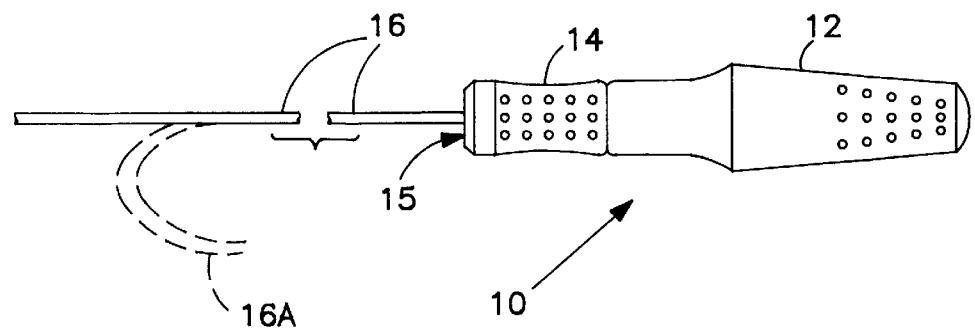
FIG. 1 is a plan view of a deflectable stylet according to the present invention.

FIG. 1 illustrates a plan view of a deflectable stylet according to the present invention. The deflectable stylet 16 is provided with a control handle assembly 10 provided with a handle 12 and a deflection control which takes the form of a spinner or knob 14, mounted rotatably and slidably with respect to the handle portion 12. The handle 12 is provided with indentations at its proximal end, as is the spinner or knob 14 to assist the physician in maintaining a grip. Ribbing, knurling or other texturing could of course be substituted. The deflectable stylet 16 exits from a proximal recess 15, within spinner or knob 14. The rotation of spinner or knob 14 causes deflection of the distal portion of stylet 16 to a curved configuration as illustrated at 16A.

Deflectable stylet 16 may take the form of any known deflectable stylet employing an outer tubular member and an inner tension wire which, when it applies tension to the distal tip of deflectable stylet 16, causes the tip of the stylet to curve. Appropriate designs for the deflectable stylet 16 include those described in the Brennen et al, Lindegren and Fideler patents discussed above and incorporated herein by reference in their entireties. Alternatively, deflectable stylet 16 may be replaced by a deflectable guidewire, for example, as disclosed in the above-cited Buchbinder patent, also incorporated herein by reference in its entirety. In all of these various guidewires and stylets, the basic structure of the deflectable stylet or guidewire consists of an outer tube which in a relaxed condition displays a generally straight configuration, and an internal tension wire coupled to the distal portion of the guidewire, and arranged such that upon application of tension to the distal tip of the guidewire or stylet, the distal portion of the guidewire or stylet exhibits a curved configuration as illustrated in broken outline at 16A.

Figure 2:
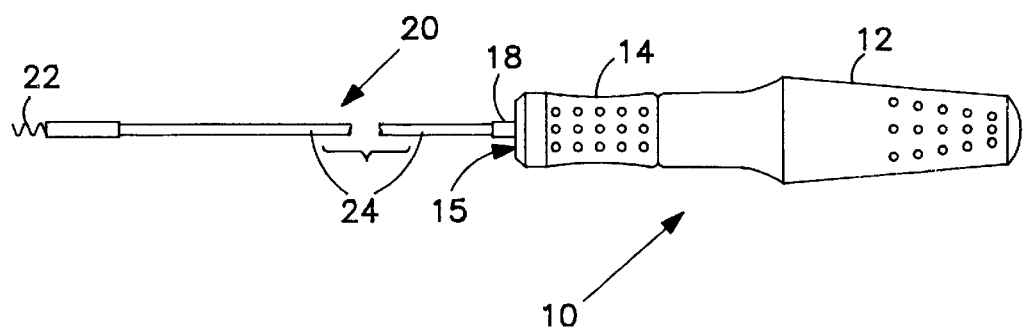
FIG. 2 is a plan view of the deflectable stylet of FIG. 1 shown inserted into an implantable cardiac pacing lead.

FIG. 2 is a plan view of the deflectable stylet of FIG. 1 inserted into a cardiac pacing lead 20. Cardiac pacing lead 20 comprises an elongated insulated lead body 24 carrying an internal conductor and provided with a connector assembly 18 located at its proximal end, which typically carries a connector pin as is typical of cardiac pacing leads. For example, the distal portion of the connector assembly 18 may correspond to the IS-1 connector standard as disclosed in U.S. Pat. No. 4,922,607 issued to Doan et al., also incorporated herein by reference in its entirety. However, other connector configurations, such as disclosed in U.S. Pat. No. 4,488,561 issued to Doring or U.S. Pat. No. 4,572,605 issued to Hess et al., both also incorporated herein by reference in their entireties, may also be employed. At the distal end of pacing lead 20 is located a fixed helical electrode 22, such as that disclosed in U.S. Pat. No. 5,473,812 issued to Morris et al. and incorporated herein by reference in its entirety, which is screwed into heart tissue in order to stimulate the heart. While the illustrated deflectable stylet is optimized for use with fixed-screw leads, it may of course also usefully be employed with any other type of stylet-guided pacing, cardioversion or defibrillation leads or with guidewire or stylet guided catheters.

As illustrated, the connector assembly 18 of the lead 20 is inserted into the distal facing opening 15 within spinner or knob 14. The spinner or knob 14 is free to rotate with respect to connector assembly 18. The internal slider member (not visible in this view) located within handle assembly 10 is free to rotate with respect to the connector pin of the lead 20. In the context of a device employing a fixed helical electrode, rotation of the entire lead with respect to the deflectable stylet is typically required in order to screw the helical electrode 22 into heart tissue.

Figure 3:
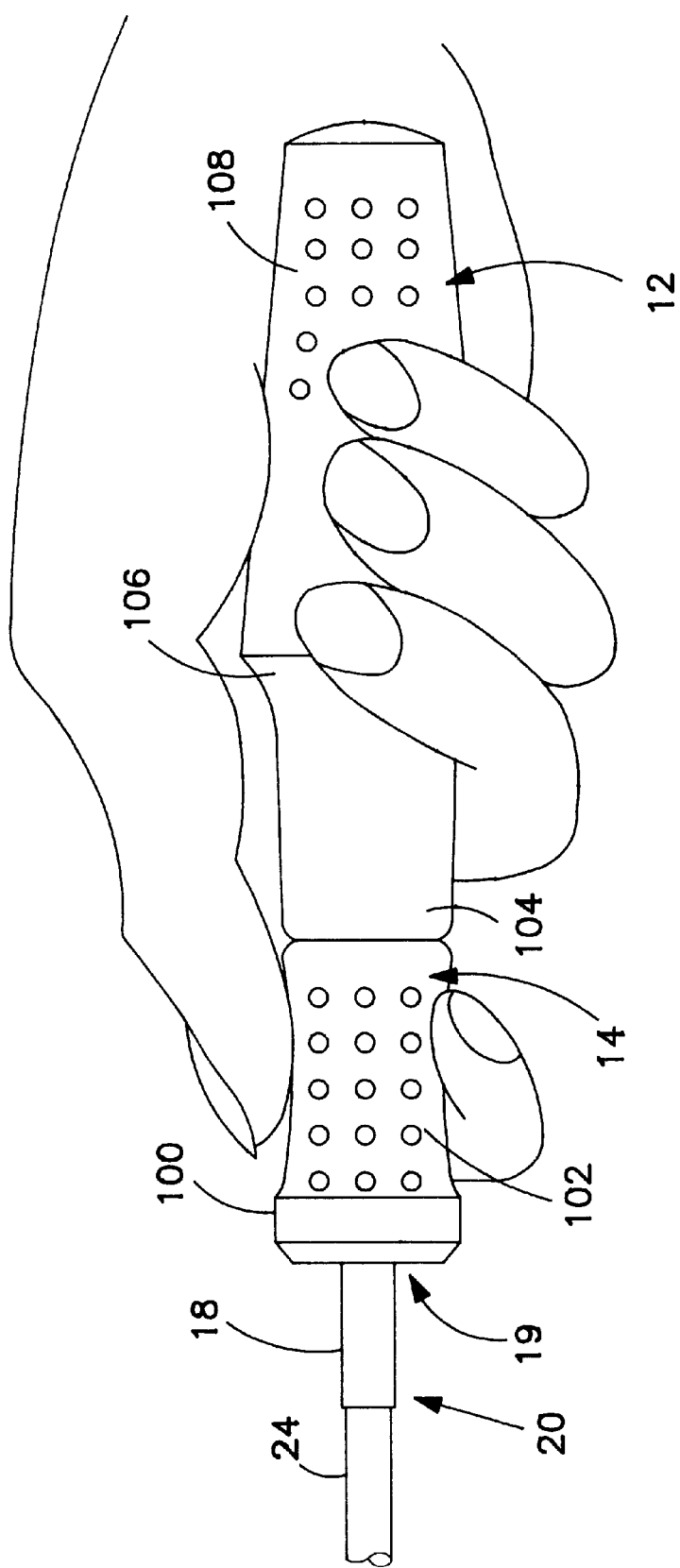
FIG. 3 is a drawing of a physician's hand and the control handle during deflection of the stylet.

FIG. 3 illustrates the handle of the deflectable stylet of FIGS. 1 and 2 in the hand of a physician, in the position in which the deflection control knob or spinner 14 is to be operated by the physician. The physician grasps the handle with his thumb and forefinger in contact with the knob or spinner 14 and his palm and other three fingers grasping the handle 12. The connector assembly 18 and the proximal portion of the lead body 24 of lead 20 are also visible, with the connector assembly inserted into the recess 15 in knob or spinner 14, and the deflectable stylet located within the lead body 24. To deflect the stylet and the lead body 24 containing the stylet, the physician either rotates knob 14 relative to handle 12 or moves the knob or spinner 14 distally with respect to the handle, to temporarily induce a curve in the stylet and lead body. The enlarged portion 100 located at the distal end of the handle or spinner 14 assists the physician in sliding the knob or spinner 14 proximally relative to the lead body.

In this view it can be seen that the knob or spinner 14 includes an enlarged distal portion 100 and a reduced diameter proximal portion 102 extending proximally to the distal end of the handle 12. The handle 12 in turn is provided with a reduced diameter portion 104, having approximately the same diameter as portion 102 of the knob or spinner 14, which extends along the handle 12 proximally to a ramped portion 106 at which point the handle substantially increases in diameter. The proximal portion of the handle 108 is tapered in a proximal direction.

As illustrated, the spinner 14 and handle 12 are sized so that the physician may comfortably grasp the handle with his thumb and forefinger engaging the knob or spinner 14 while the physician's palm and other three fingers are arranged along the handle 12. The length of the handle may be in the range of 2½ to 4½ inches, with the total length of the reduced diameter portions 102 and 104 of the knob 14 and the handle 12 together extending over a length of about 1½ to 3 inches. In a particular preferred embodiment the overall length of the control handle assembly is a little less than 5 inches and the overall length of the reduced diameter portions is a little less than 2 inches. As illustrated in FIG. 3, the diameter of the proximal portion 102 of the knob 14 and the adjacent reduced diameter portion 104 of the handle 12 need not be precisely constant. As illustrated, the diameter increases slightly along the length of both of these portions of the control handle assembly, as one moves proximally along the handle.

Figure 4:
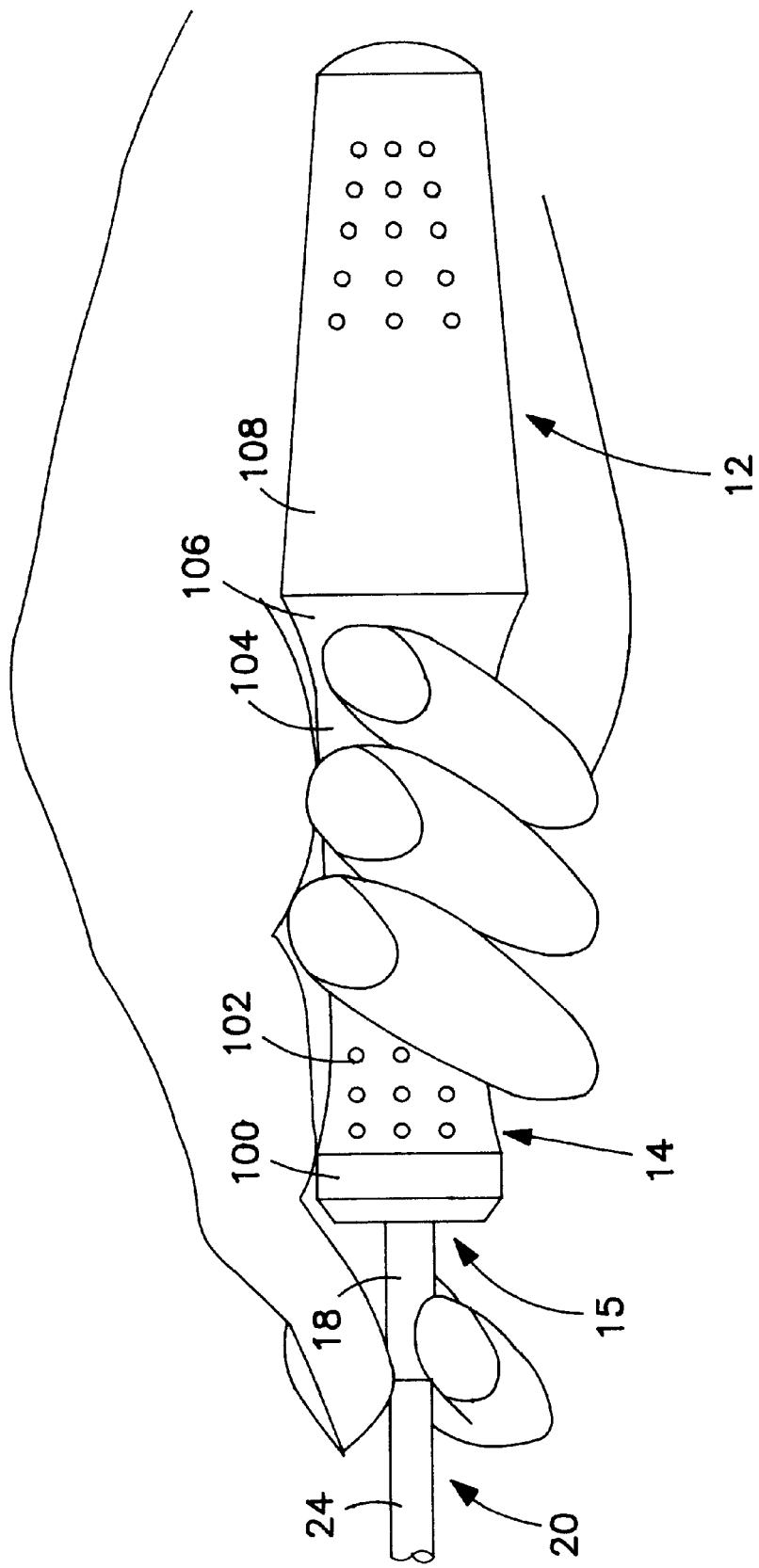
FIG. 4 is a drawing of a physician's hand and the control handle during rotation of the lead around the stylet.

FIG. 4 is a picture of the control handle and the physician's hand illustrated in FIG. 3, with the physician's hand positioned to rotate the lead body 24 around the deflectable stylet so that the helix 22 (FIG. 2) of the lead may be screwed into body tissue. The physicain may also employ this position to counter-rotate the lead body during advancement or to disentangle the fixation helix from tricuspid valve structures. In this position, it should be noted that the physician's thumb and forefinger are arranged to grasp the proximal portion of the lead body and/or the connector assembly 18, while at least the physician's index and ring fingers and palm are arranged around the reduced diameter portions 102 and 104 of the knob 14 and handle 12. Because the diameters of the knob 14 and handle 12 at their juncture are essentially identical, and because the overall diameter in the area in which the physician's index and ring fingers lie is generally constant, the physician's grasp inherently operates to stabilize the location of the knob 14 relative to the handle 12, so that whatever desired curve the physician has chosen to impart to the stylet remains unchanged during the process of screwing the helical electrode 22 (FIG. 1) into body tissue. This in turn prevents inadvertent contact of the physician's thumb or forefinger with the knob or spinner 14 from changing the degree of deflection of the stylet and in turn dislodging the lead prior to completion of a process of affixing it to body tissue.

Figure 5:
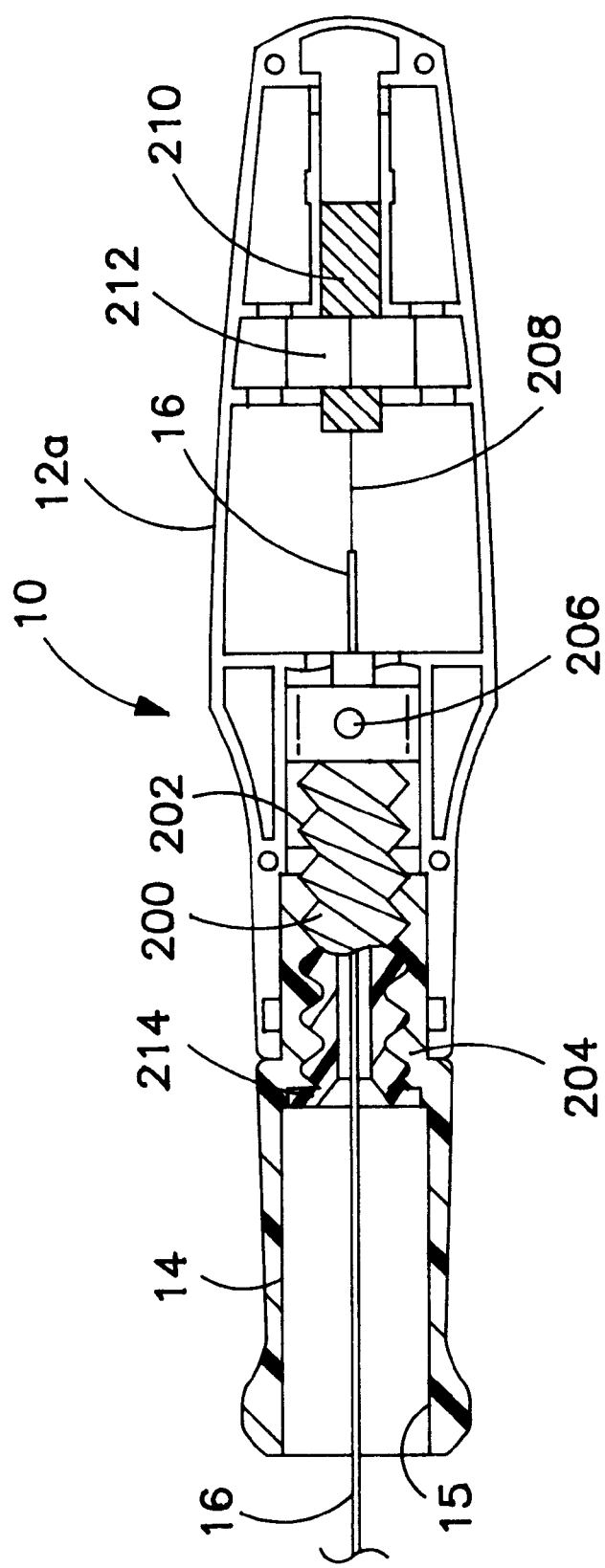
FIG. 5 is a cut-away view through a partially disassembled control handle of the deflectable stylet illustrated in FIG. 1.

FIG. 5 is a cutaway view of a partially disassembled control handle 10, as illustrated in the figures discussed above. The handle 12 is fabricated of two molded plastic parts, joined together essentially along a longitudinal line extending the length of the handle. One of the two handle halves 12A is illustrated in conjunction with the knob or spinner 14, showing cross-section and the internal slider 200, not visible in the previous illustrations. The internal, distally facing recess 15 in knob 14 is visible in this view, and is sized to be of sufficient length that it inherently serves as a strain relief to the deflectable stylet 16, preventing kinking or bending of the stylet at the point it exits the slider 200. Recess 15 also assists in assisting the physician in repositioning his hand when moving between proximal and distal positions relative to the handle, in that the portion of the connector assembly distal to the connector pin is immediately adjacent the distal end of the knob.

The slider 200 generally takes the form of a rod provided with external threading 202 which engage internal threading 204 within knob 14. At the proximal end of the slider 200 are pins 206, which engage corresponding grooves in the molded handle halves, not visible in this drawing, which in turn prevent rotation of the slider 200 relative to the handle. Thus, rotation of the knob 14 relative to the handle causes longitudinal movement, but not rotational movement of the slider 200. The outer tube of deflectable stylet 16 is mechanically coupled to the slider 200, while the tension wire 208 within the stylet 16 is anchored to the handle. Thus, on distal movement of the slider 200 relative to the handle 12A, the outer tube of the stylet is moved with respect to the tension wire 208, causing tension wire 208 to apply tension to the tip of the stylet and deflecting it, in the manner described above in the various cited patents pertaining to deflectable stylets. Tension wire 208 is anchored to a threaded rod 210 which is adjusted longitudinally by means of a hex nut 212, which is fixedly mounted in the handle.

As illustrated, the knob 14 and the slider 202 may be slid distally with respect to the handle as a unit, providing an alternative mechanism for applying tension to tension wire 208 and deflecting stylet 216. Deflection of the stylet by this mechanism is convenient in the case in which the physician wants to only very briefly and very quickly induce a curve to facilitate entry of the lead into a desired location, for example, into the coronary sinus or for navigating the lead through the vena cava and through the tricuspid valve.

In the embodiment illustrated, the slider is provided with an internal bore 214 which may receive the connector pin of an implantable lead. In this case, the bore 214 should be of larger diameter than the connector pin, so that the lead may be rotated with respect to the stylet 216. Alternatively, the bore 214 may be omitted, with the connector pin simply lying adjacent the distal end of the slider 202.

The above disclosed embodiment should be considered exemplary rather than limiting with regard to the scope of the claims that follow.

In conjunction with the above specification, we claim:

1. A control handle assembly for use with a deflectable stylet or guidewire, comprising:

a handle having a proximal portion and a distal portion, the proximal portion being of increased diameter relative to the distal portion; and a deflection control located adjacent the distal portion of the handle and extending distally therefrom, the control being movable relative to the handle, the handle assembly further comprising means for deflecting the stylet or guidewire responsive to movement of the deflection control relative to the handle; and wherein the deflection control has a proximal portion having a diameter corresponding to the diameter of the distal portion of the handle, the proximal portion of the deflection control and the distal portion of the handle together defining a segment of the handle assembly of reduced diameter relative to the proximal portion of the control handle and extending for a distance of at least about one and one half inches along the control handle assembly whereby at least two fingers of a typical physicians hand may conveniently simultaneously grasp the handle and deflection control, stabilizing deflection control relative to the handle.

2. A handle assembly according to claim 1 wherein the segment of the handle assembly of reduced diameter relative to the proximal portion of the control handle extends for one and one half to three inches along the control handle assembly.

3. A handle assembly according to claim 1 wherein the handle extends for a distance of one and one half to three inches along the control handle assembly.

4. A handle assembly according to claim 1 wherein the handle extends for at least two and one half inches.

5. A handle assembly according to claim 1 wherein the handle extends for two and one half to four and one half inches.

* * * * *